United States Patent [19]
Hayashi

[11] Patent Number: 5,973,330
[45] Date of Patent: Oct. 26, 1999

[54] FLUORESCENCE DETECTION APPARATUS

[75] Inventor: Hidechika Hayashi, Kanagawa, Japan

[73] Assignee: Tosoh Corporation, Yamaguchi, Japan

[21] Appl. No.: 08/898,785

[22] Filed: Jul. 23, 1997

[30] Foreign Application Priority Data

Jul. 24, 1996 [JP] Japan ................................. 8-194593

[51] Int. Cl.⁶ ........................ G01N 21/64; G01N 33/573
[52] U.S. Cl. ................ 250/458.1; 250/353; 435/288.7; 356/317
[58] Field of Search ............................... 250/458.1, 353, 250/461.1, 459.1; 356/417, 317, 318; 435/288.7

[56] References Cited

U.S. PATENT DOCUMENTS

| | | | |
|---|---|---|---|
| 4,896,961 | 1/1990 | Ito | 356/417 |
| 5,059,010 | 10/1991 | Yomoda . | |
| 5,260,764 | 11/1993 | Fukuda et al. | 356/318 |
| 5,296,703 | 3/1994 | Tsien | 356/318 |
| 5,460,943 | 10/1995 | Hayashi et al. | 435/7.4 |
| 5,480,775 | 1/1996 | Ito et al. | 356/318 |
| 5,677,134 | 10/1997 | Hayashi et al. | 356/320 |
| 5,738,997 | 4/1998 | Hayashi et al. | 356/318 |

FOREIGN PATENT DOCUMENTS

| | | |
|---|---|---|
| 0252 683 A2 | 1/1988 | European Pat. Off. . |
| 0 521 636 | 1/1993 | European Pat. Off. . |
| 0521 636 A1 | 1/1993 | European Pat. Off. . |
| 0 585 754 | 3/1994 | European Pat. Off. . |
| 585 754 A1 | 3/1994 | European Pat. Off. . |
| 2 215 838 | 9/1989 | United Kingdom . |
| 2215838 | 9/1989 | United Kingdom . |
| 92/13264 | 8/1992 | WIPO . |
| WO 92/13264 | 8/1992 | WIPO . |

*Primary Examiner*—Constantine Hannaher
*Assistant Examiner*—Darren M. Jiron
*Attorney, Agent, or Firm*—Jeffrey I. Auerbach; Elliot C. Mendelson; Howrey & Simon

[57] ABSTRACT

A fluorescence detection apparatus is provided which has a partial reflection mirror 8 for transmitting a part of fluorescence light emitted from a fluorescent substance by projecting excitation light and reflecting the rest of the fluorescence light, and a pair of a first and a second photodiode 2,3 for measuring the light transmitted through or reflected by partial reflection mirror 8 respectively at a selected wavelength, and the pair of the first and the second diodes are arranged to be optically equivalent relative to the partial reflection mirror 8. This fluorescence detection apparatus is affected less by positional deviation of the measurement cell relative to the optical measurement system.

11 Claims, 5 Drawing Sheets

FLUORESCENCE DETECTION APPARATUS

BACKGROUND OF THE INVENTION

1. Field of the Invention

The present invention relates to a fluorescence detection method, and a fluorescence detection apparatus useful for immunoassay. Particularly the present invention relates to a fluorescence detection method and an apparatus for determining the concentration of an objective substance with high accuracy by measuring the fluorescence from the objective substance and the fluorescence from a reference substance.

2. Description of the Related Art

Methods of immunoassay are known which utilize a fluorescent label contained in a immunocomplex or a fluorescent product formed by a labeling substance. Of these methods, enzyme-labeled immunoassay is conducted, for example, by bringing into contact a serum sample containing an objective substance and an antibody labeled by an enzyme with an antibody immobilized on a solid phase to form an immunocomplex, removing the unreacted portion of the enzyme-labeled antibody, adding a substrate for the enzyme contained in the complex to cause an enzyme reaction, and measuring the fluorescence emitted from the fluorescent substance formed by the enzyme reaction.

The conventional fluorescence detection apparatus for such a detection method comprises an exciting light irradiation system having a light source and a lens, and an optical measurement system comprising at least one detection element and at least one lens for measuring the fluorescence emitted from an objective substance (fluorescent substance). The optical system is selected to have the direction of the projected exciting light (illuminating light) so as to coincide substantially with, or to be perpendicular to the converging direction of the emitted fluorescence, depending on the measurement cell type and the surrounding conditions. In the optical system having the exciting light direction coinciding with the fluorescent light emission direction, a partial reflection mirror such as a dichroic mirror is employed to separate the fluorescent light from the exciting light.

The conventional detection apparatuses have disadvantages such that the measurement accuracy is not sufficient owing to variation of the measured value caused by change of the meniscus of the sample surface or by the presence of bubbles, and that the linear dependence of the fluorescence intensity on the concentration of the objective substance is impaired, at high concentrations, owing to absorption of the exciting light by the objective substance, causing the drop of the intensity of the generated fluorescence.

To offset such disadvantages, a method is proposed (JP-A-5-38297 and its corresponding U.S. Pat. No. 5,460,943). In this method, a reference fluorescent substance is added which is excited at the same wavelength as the objective substance in the sample and emits fluorescence of a wavelength different from that of the objective measurement substance, and the fluorescent light intensities of the sample and the reference substance are measured to obtain the concentration of the objective substance. This method, which utilizes different fluorescence wavelengths, may be called a two-wavelength fluorometry. For example, in this method, the fluorescence light is separated into two fluorescence light beams by a partial reflection mirror such as a dichroic mirror, the separated fluorescence light beams are respectively allowed to pass through a wavelength selection element, thus the fluorescence from the objective substance and the fluorescence from the reference substance are detected selectively, the intensities of the respective fluorescence light are measured, and the measured value of the fluorescence light of the objective substance is corrected based on the change of the fluorescence light of the reference substance.

The two-wavelength fluorometry enables high accuracy measurement. The inventors of the present invention made studies to improve the accuracy further, and found that the ratio of the changes of the signals of the two fluorescence intensities are not always constant in measurement of many samples in the aforementioned conventional two-wavelength fluorometry.

The variation of the ratio of the signal changes was found to be due to the causes below. For example, in the apparatus for immunoassay for quantitative determination of a biological substance, enzyme-containing complexes are placed usually in relatively small cells, and a large number of such cells are delivered mechanically and automatically into an optical measurement station for the quantitative determination. However, it is not easy to deliver constantly the cells without positional variation precisely to the predetermined position in the measurement station. In particular, in commercial apparatuses utilizing a large number of measurement cells, it is extremely difficult to reproducibly position each cell with respect to the optical measurement system. The positional variation of the cells occurs unavoidably. Furthermore, bubbles can be formed in the measurement liquid in dispensing the enzyme substrate into the measurement cell, and the bubble formation cannot be completely prevented. The variation of the signal change ratio of the aforementioned two detection elements, by this positional deviation and the bubble formation makes impossible the complete correction for the positional deviation. When the cell deviates positionally or bubbles are formed in the cell, the ratio of the signal changes of the two detectors is not constant in the two-wavelength fluorometry owing to physical non-equivalency such as positional deviations of the detection elements, of the apertures before the respective detection elements, and of the optical axes of the respective detection elements, and sensitivity irregularity of the detection elements, thereby causing inconformity of the change ratios of the detection signals with the two detection elements.

In the case where the intensity of the fluorescence from the reference substance is affected more by the positional deviation of the cell than that from the measurement object substance, the measurement data corrected by the same procedure (by use of a correction equation, or the like) involves the influence of the positional deviation.

SUMMARY OF THE INVENTION

An object of the present invention is to provide an apparatus for fluorescence detection and enzyme activity measurement which is affected less by the positional deviation of the measurement cell relative to the optical system of the apparatus without the above disadvantages of conventional methods.

According to an aspect of the present invention, there is provided a fluorescence detection apparatus having a light-separating element for transmitting a part of fluorescence emitted from a fluorescent substance by projection of excitation light and reflecting the rest of the fluorescence, and a pair of a first detection element and a second detection element for measuring the fluorescence transmitted through or reflected by the light-separating element respectively at a selected wavelength, wherein the pair of the detection elements are arranged to be optically equivalent to each other relative to the light-separating element.

According to another aspect of the present invention, there is provided a fluorescence detection apparatus for measuring a fluorescent substance formed in a reaction cell by reaction caused by an enzyme contained in an immunocomplex or a fluorescent substance contained in a complex formed by immunoreaction, comprising optical light source system for projecting light for exciting a fluorescent substance in the cell, a light-separating element for transmitting a part of fluorescence emitted from a fluorescent substance and reflecting the rest of the fluorescence, and a pair of a first detection element and a second detection element for measuring selectively the fluorescence transmitted through or reflected by the light-separating element, and a first condensing element and a second condensing element placed on the optical path for introducing the fluorescence of the fluorescent substance to the light-separating element, wherein the first condensing element and the second condensing element are arranged such that the image of the fluorescent substance is formed by the first condensing element on the second condensing element, and the image of the first condensing element is formed by the second condensing element on each of the first detection element and the second detection element, and the pair of the detection elements are arranged to be optically equivalent to each other relative to the light-separating element.

DETAILED DESCRIPTION OF THE PREFERRED EMBODIMENT

The fluorescence detection apparatus of a first embodiment of the present invention has a light-separating element for transmitting a part of fluorescence light emitted from a fluorescent substance by projection of ex citation light and reflecting the rest of the fluorescence light, and a pair of a first detection element and a second detection element for measuring selectively the light transmitted through or reflected by the light-separating element respectively at a selected wavelength, the pair of the detection elements being arranged to be optically equivalent to each other relative to the light-separating element.

In the above, "being arranged to be optically equivalent" means that the two detection elements are arranged such that the changes of the output signals are at nearly the same levels (the change rates being as close as possible), when the cell deviates positionally.

The light-separating element includes partial reflection mirrors such as dichroic mirrors, and combination prisms, and may be any article which transmits a part of fluorescence light and reflects the rest of the fluorescence light. A transparent plate such as an optical glass plate and a quartz glass plate are useful therefore when the intensity of the fluorescence is sufficiently high. Generally, however, a partial reflection mirror such as a dichroic mirror is preferably used since it introduces the fluorescence light to the detection elements with high efficiency. The transparent plate or the dichroic mirror is placed at an angle of 45° to the optical axis. The element plate is preferably thinner, since the thickness causes deviation of the optical axis, and has usually a thickness of about 1 mm. A combination prism constituted of two isosceles right triangle prisms glued together at the hypotenuse faces is suitable for achieving highly precise equivalence because the prism does not cause deviation of the optical axis of the transmitted light. Wavelength selectivity can be achieved by forming a multi-layered film at the glued interface.

The detection element includes photodiodes and photomultipliers, but is not limited thereto.

The fluorescence detection apparatus of this first embodiment is characterized by a pair of detection elements arranged to be optically equivalent to each other relative to the light-separating element. Aforementioned "optically equivalent to each other" does not mean the complete equivalency in all the optical conditions, but means the arrangement of the two detection elements to equalize the changes of output signals from the two detection elements (to minimize the difference between the change ratio) when the cell diviates positionally.

With the aforementioned arrangement of the pair of the first and second detection elements, the ratio of the changes in the detection elements can be made substantially constant in every respect, (the ratio of the fluorescent quantities can be made substantially constant regardless of the positional deviation of the reaction cell), and thereby the intensity of the fluorescence can be measured with high accuracy without the aforementioned influence of positional deviation of the reaction cell.

In a modification of the above fluorescence detection apparatus, a first light-condensing element and a second-light condensing element are arranged in this order on the optical path of introducing the fluorescence light from the fluorescent substance to the light-separating element. Thereby, the image of the fluorescent substance is formed by the first condensing element on the second condensing element, and the image of the first condensing element is formed by the second condensing element on each of the first detection element and the second detection element.

The fluorescence detection apparatus of another embodiment of the present invention is an apparatus for measuring a fluorescent substance formed in a reaction cell by reaction caused by an enzyme contained in an immunocomplex, or a fluorescent substance contained in a complex formed by immunoreaction, comprising optical light source system for projecting light for exciting a fluorescent substance in the cell, a light-separating element for transmitting a part of fluorescence emitted from a fluorescent substance and reflecting the rest of the fluorescence, and a pair of a first detection element and a second detection element for measuring selectively the light transmitted through or reflected by the light-separating element, and a first condensing element and a second condensing element placed on the optical path for introducing the fluorescence of the fluorescent substance to the light-separating element, wherein the first condensing element and the second condensing element are arranged such that the image of the fluorescent substance is formed by the first condensing element on the second condensing element, and the image of the first condensing element is formed by the second condensing element on each of the first detection element and the second detection element, and the pair of the detection elements are arranged to be optically equivalent to each other relative to the light-separating element. The light-separating element may be placed between the first condensing element and the second condensing element. In this arrangement, two of second condensing elements are employed and one is provided between the light-separating element and the first detection element, and another is provided between the light-separating element and the second detection element.

In a modification of this second embodiment, the measurement is conducted for a fluorescent substance formed by enzyme contained in an immunocomplex (hereinafter referred to as a "formed fluorescent substance") and for a reference fluorescent substance emitting fluorescence without enzymatic action. One of the detection elements measures selectively the fluorescence at the fluorescence wavelength of the formed fluorescent substance, and the other of the detection elements measures selectively fluorescence at the fluorescence wavelength of the reference fluorescent substance.

The formed fluorescent substance formed by enzyme reaction, and the reference fluorescent substance insensitive to the enzyme reaction in the present invention are exemplified by the substances mentioned, for example, in the aforementioned JP-A-5-38297 and its corresponding U.S. Pat. No. 5,460,943. An example of the formed fluorescent substance is 4-methylumbelliferone (formed fluorescent substance) formed from 4-methylumbelliferyl phosphate by enzyme reaction such as alkaline phosphatase. This 4-methylumbelliferone emits fluorescence with a peak at about 450 nm by exciting light of 365 nm in an alkaline medium (around pH 10). On the other hand, the reference fluorescent substance is exemplified by dansyl-L-alanine which emits fluorescence having a peak at about 550 nm under the same conditions (pH, exciting light wavelength) as above.

In another modification of this second embodiment of the present invention, the fluorescent substance is a label contained in a complex resulting from the immunoreaction of a measurement object substance.

The light source employed in the embodiments of the present invention includes electric discharge tubes, fluorescent lamps, and the like. The influence of disturbing light can be eliminated by using a modulated light source and detecting synchronously with the detection element (light receiving side).

An aperture is preferably provided near the detection element or the light source to limit the optical path. For example, a round aperture provided near the rectangular detection element to limit the detection face smaller will decrease the change of reflected light caused by the reaction cell wall when the reaction cell deviates from the prescribed position.

With such a constitution in which a sample, a first condensing element, a second condensing element, and a pair of detection elements are arranged as mentioned above, even when the reaction cell deviates positionally, the projected light intensities change at a constant ratio in every point in the first and the second detection elements. Therefore, the intensity of fluorescence of the fluorescent substance formed by enzyme contained in immunocomplex and the intensity of the fluorescence of the reference fluorescent substance can be measured, while the ratio is constant, without influence of positional deviation of the measurement cell. Thus, the ratio of the fluorescence intensity of the reference fluorescent substance which does not change with time, and the fluorescence intensity of the formed fluorescent substance which changes with time can be measured as the optical information by a pair of detection elements provided in optical equivalency with high accuracy with little influence of the positional deviation of the cell.

In the fluorescence detection apparatus of the present invention as described above, wavelength selection in the optical detection system can be conducted by a wavelength-selecting element provided on the optical path from the light-separating element to the detection element. The wavelength selection of the transmitted light can be conducted also by imparting the wavelength selection function to the light-separating element. A filter is employed usually as the wavelength selection element. For example, in front of the one detection element, a filter is provided which transmits the fluorescence from the objective substance but intercepts the fluorescence from the reference fluorescent substance, and in front of the other detection element, another filter is provided which transmits the fluorescence from the reference fluorescent substance but intercepts the fluorescence from the objective substance. The filter includes band-pass filters, and cut-off filters. An interference filter, which is a kind of band-pass filter utilizing interference membrane, is useful for wavelength selection of a fluorescence detector because of the sharp selection characteristics thereof. For selection of longer wavelength portion of fluorescence from the measurement object, a cut-off filter is useful as well as an interference filter. With a light source having broad wavelength distribution, a wavelength selection element is preferably provided on the optical path of the exciting light source to eliminate unnecessary wavelength light. An interference filter, or a colored glass band filter is useful therefor. The desired filter characteristics may be obtained by a single filter, by a combination of light-separating elements having light selectivity, by combination of light separating element and filters, or by combination of plural filters. The required wavelength selectivity of the above filters depends on the required detection accuracy, and is not necessarily required to transmit only the detection wavelength light. The selectivity is sufficiently provided that the fluorescence of the formed fluorescent substance and that of the reference fluorescent substance can be detected separately.

In the fluorescence detection apparatus of the present invention as described above, a condensing element for projecting the light source image to the cell, and the first and second condensing elements for projection of the image of the fluorescent substance in the cell as above are provided on respective optical paths. The functions of the above first condensing element and the condensing element of the light-source optical system may be fulfilled by a single element, or by separate elements. Usually a lens is employed as the light condensing element. The curvature radius of the lens is selected suitably depending on the position of the image, and the aperture diameter is selected suitably depending on the spreading of the employed light. The lens system is constituted of two lens units. Each lens unit may be a single lens or a combination lens. The lens may be a double convex lens or a plano-convex lens. The lens system is selected in consideration of spherical aberration. In the present invention, "projection of the image" means not only the formation of a complete image but also formation of incompletely focused blurred image.

The present invention is not limited to the above embodiments, and includes other necessary constitutions.

The optical axis of the projecting excitation light and the optical axis of the fluorescence emission may be designed to coincide with each other, or to be perpendicular to each other.

The fluorescence intensity of the formed fluorescent substance is corrected in various means according to the measured fluorescence intensity of the reference fluorescent substance in the present invention. One example is a constitution employing a microprocessor unit (MPU) having a program of the necessary computing equation. The correction system, in addition to the computing system, includes comparison with a predetermined calibration curve, readout of the memorized information from the memory means (ROM, etc.), and the like.

In the present invention, a reference fluorescent substance, which does not change in its quantity with time, is allowed to coexist with the formed fluorescent substance which changes in its quantity with time by enzyme reaction in a cell. The intensities of the fluorescence at two wavelengths emitted from the cell are measured by a pair of detection elements which are placed to be optically equivalent. The measured intensity of the fluorescence emitted from the fluorescent substance formed by enzyme reaction is corrected according to the change of the fluorescence intensity of the reference fluorescent substance which does not change its quantity and maintains the fluorescence intensity constant inherently, whereby the true quantity of the formed fluorescent substance is derived.

Figure 1:
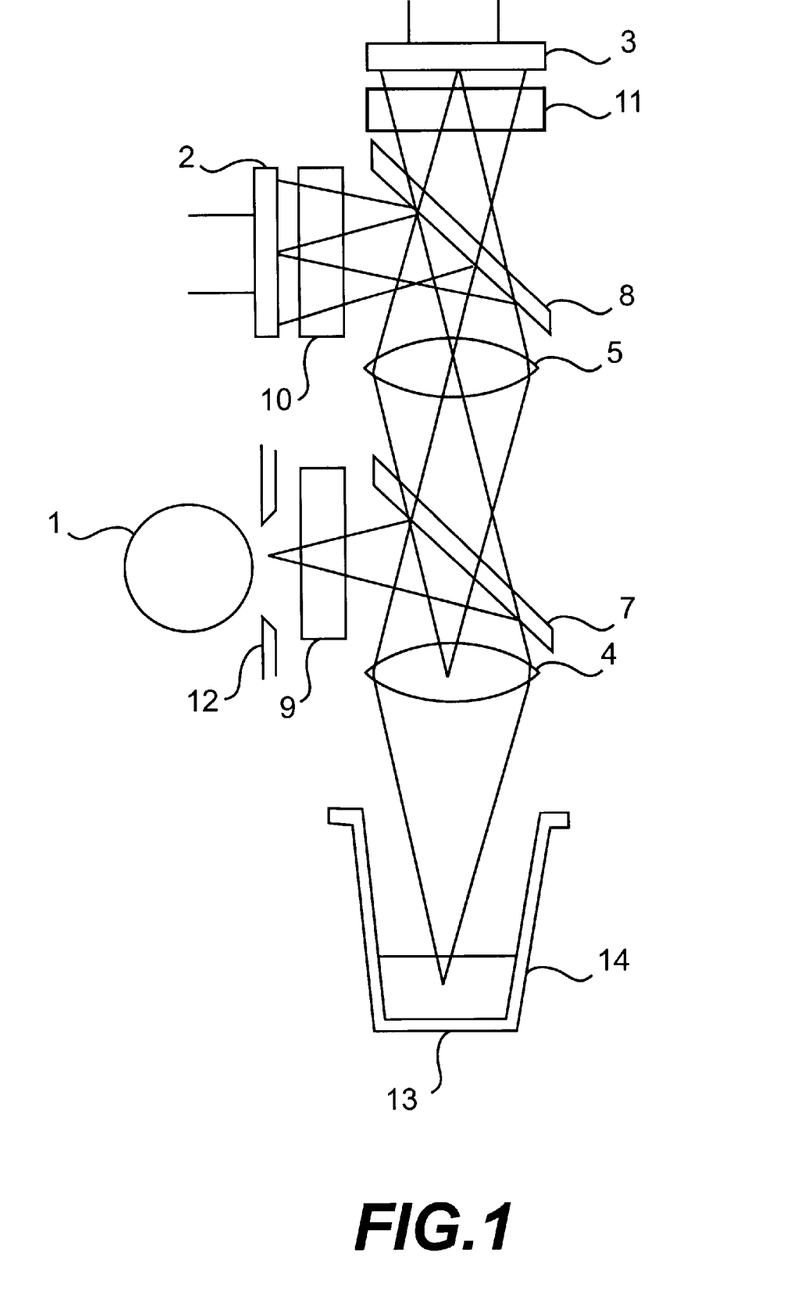
FIG. 1 is a front view showing schematically the constitution of the enzyme activity measurement apparatus (fluorescence detection apparatus) of a first embodiment of the present invention.

FIG. 1 illustrates schematically an example of constitution of the fluorescence detection apparatus (enzyme activity measurement apparatus of the present invention). A light source 1 projects exciting light through a light source aperture 12, a filter 9 as the wavelength-selecting element, a partial reflection mirror (half mirror) 7, and a lens 4 as the condensing element to form a light source image (the image of light source itself, or the image of light source) in a cell 13.

The cell 13 contains immunocomplex formed by immunoreaction of a biological substance, labeled antibody with immobilized antibody. Into the cell, a substrate is injected which forms a fluorescent substance by enzyme reaction contained in the complex. Subsequently the cell is delivered to the position shown in the drawing by a delivery mechanism not shown in the drawing, and is fixed there for the intended measurement. An enzyme-insensitive reference fluorescent substance may be preliminarily fixed in the solid phase in the cell, may be injected simultaneously with the substrate, or at other time prior to the measurement, or may be added preliminarily to the substrate solution. The numeral 14 indicates the liquid containing the fluorescent substances in the cell 13.

As described above, the cell 13 is delivered to the fluorescence measurement position. When exciting light is projected from the light source 1, the fluorescent substance which is produced by enzyme reaction and is accumulated, and the reference fluorescent substance which is not affected by the enzyme are excited to generate fluorescence. This fluorescence was allowed to pass through the lens 4, the partial reflection mirror 7, and the lens 5. A part of the fluorescence is reflected by the partial reflection mirror 8, and the rest of the fluorescence passes through the partial reflection mirror 8. The fluorescence reflected by the partial reflection mirror is introduced to the filter 10, and the prescribed wavelength of the fluorescence is projected to the photodiode 2. The fluorescence transmitted through the partial reflection mirror is introduced to the filter 11, and the selected wavelength of the fluorescence is projected to the photodiode 3.

In the above constitution, the lens (first condensing element) 4 and the lens (second condensing element) 5 are arranged on the optical path of the fluorescence from the cell to the light-separating element such that the image of the fluorescent substance is formed by the lens 4 on the lens 5, and the image of the lens 4 is formed by the lens 5 on each of the photodiode (first detection element) 2 and the photodiode (second detection element) 3. An aperture is preferably provided in front of the photodiodes 2, 3 respectively (not shown in the drawing). For example, circular apertures of 5 mm diameter in front of the respective detection elements having a square light-receiving face of 6 mm×6 mm will effectively offset the influence of the side wall of the reaction cell caused by positional deviation of the reaction cell.

The arrangement of the pair of photodiodes 2, 3 as above equalizes substantially (or minimizes the difference of) the ratio of the change of the fluorescence projected to any points of the each photodiodes from the cell through the optical projection system (including lens 4, partial reflection mirror 7, lens 5, and partial reflection mirror 8). Thereby the difference in the signal change rates can be significantly reduced which may be caused by the positional deviation of the cell relative to the optical measurement system (in FIG. 1, positional deviation in the lateral direction on the plain of the drawing, and in the perpendicular direction thereto).

The signals corresponding to the fluorescence intensities measured by the photodiodes 2, 3 are transferred to an MPU not shown in the drawing for correction treatment to determine the quantity of the fluorescent substance formed by enzyme reaction and accumulated, or the amount of the enzyme contained in the immunocomplex substantially, and thereby to determine the physiologically active substance in the sample.

Figure 4:
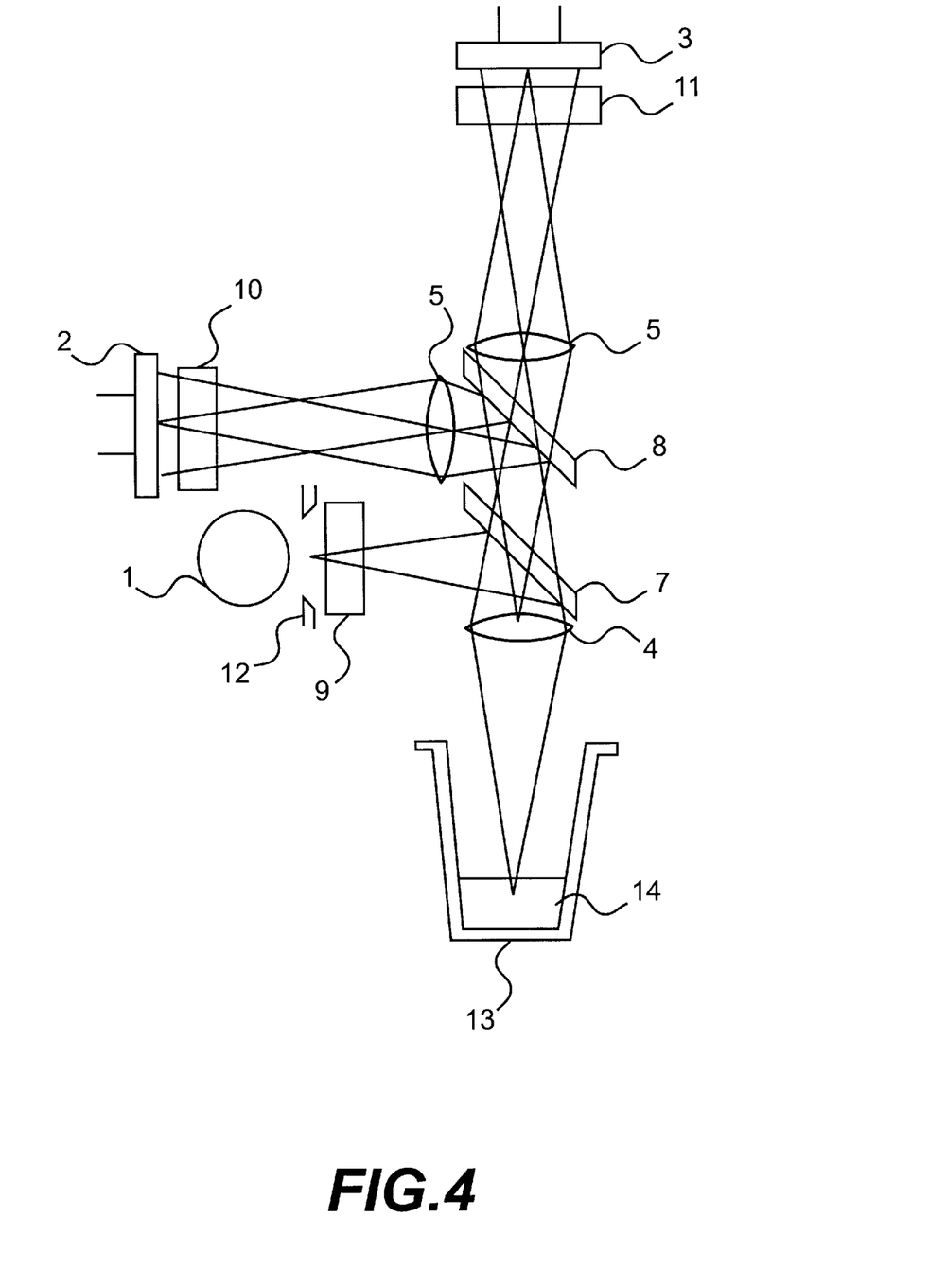
FIG. 4 shows a modification example of the apparatus of FIG. 1.

In FIG. 1, the lens (second condensing element) 5 is provided before the partial reflection mirror 8 in the optical path of the light projection. Instead, the same effect can be achieved by providing the lenses 5 behind the partial reflection mirror 8 as shown in FIG. 4. In FIG. 4, the same reference numbers as in FIG. 1 are used for indicating the corresponding member.

Figure 2:
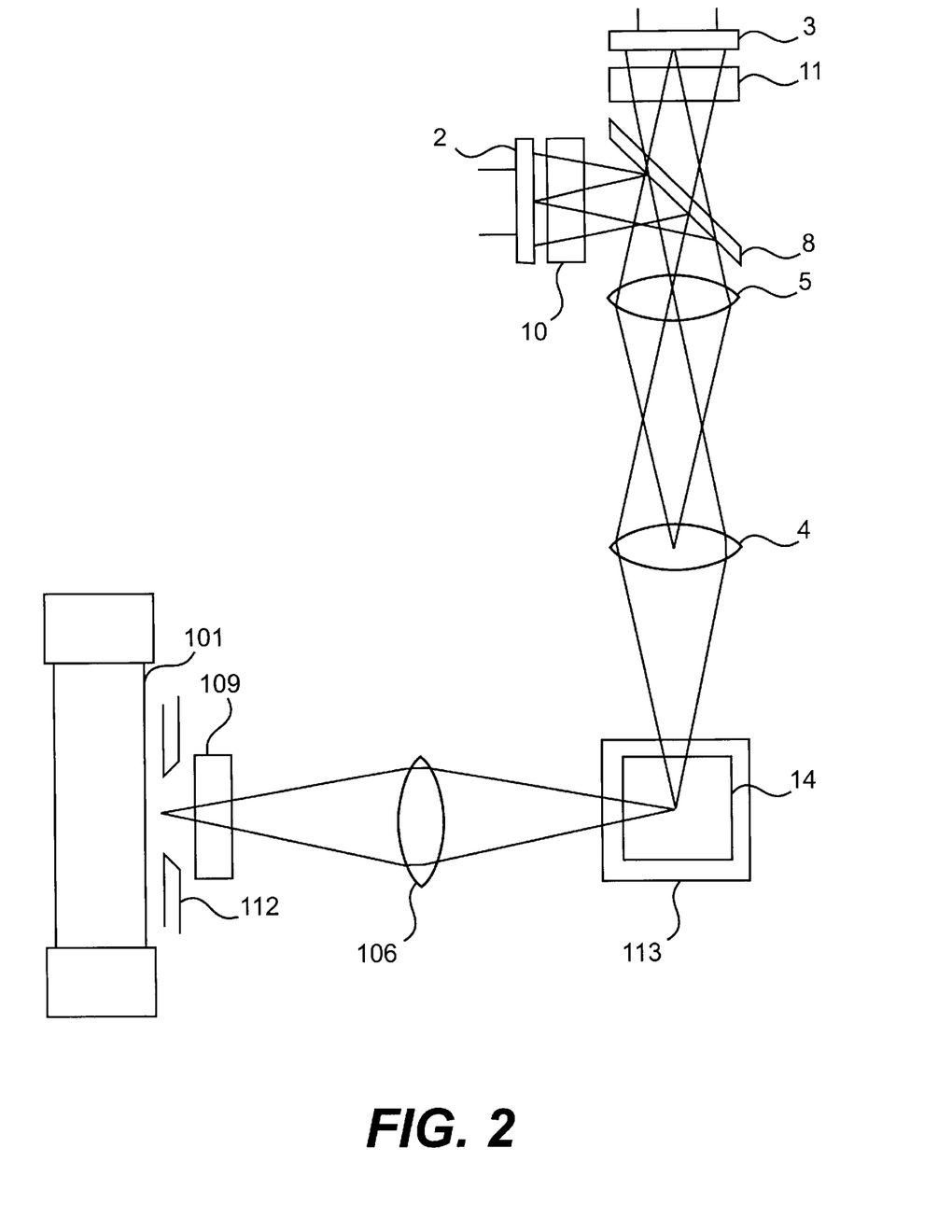
FIG. 2 is a front view showing schematically the constitution of the enzyme activity measurement apparatus (fluorescence detection apparatus) of a second embodiment of the present invention.

FIG. 2 is a plane view showing schematically another example of the constitution of an enzyme activity measurement apparatus (fluorescence detection apparatus). In this example, the optical paths of the light source system and the measurement system are arranged to be perpendicular to each other. The same reference numbers as in FIG. 1 are used for indicating the articles corresponding to the ones in FIG. 1 without explanation.

In this example, a long fluorescent lamp is used as the light source 101, and the exciting light is projected therefrom through an aperture 112, a filter 109, and a lens 106 different from the above lens 4 to the cell (made from a transparent material) 113. The image of the light source is formed by the lens 106 nearly entirely in the cell, and the image of the fluorescent substance is formed by the lens 4 on the lens 5. Further, nearly the entire of the image of the lens 4 is formed on each of the detecting faces of the pair of the photodiodes 2, 3 by the lens 5.

This apparatus gives the same effect as the one shown in FIG. 1, and a further additional effect such that a single light source 10 can be used commonly for plural juxtaposed fluorescence detection apparatus.

Figure 5:
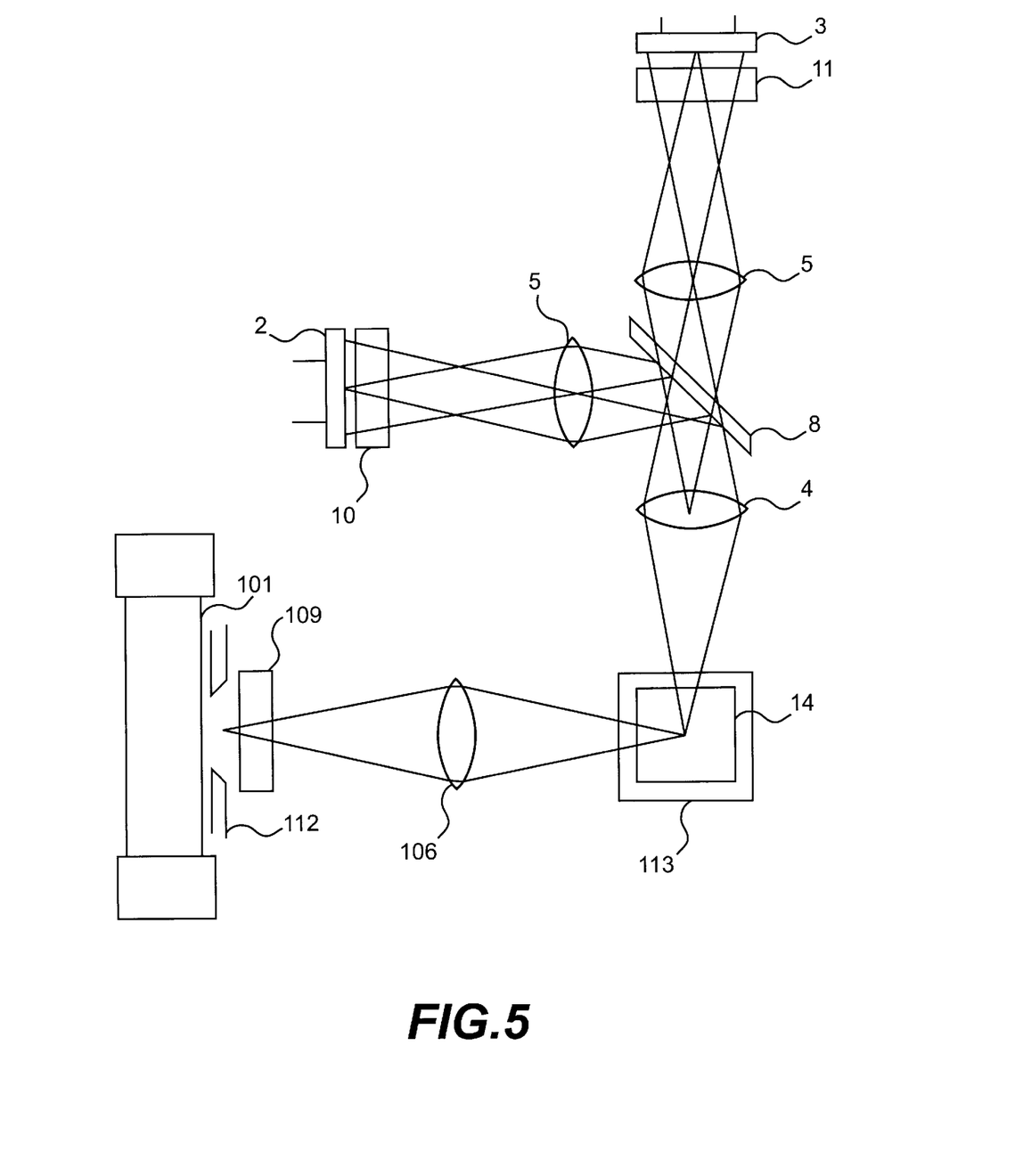
FIG. 5 shows a modification example of the apparatus of FIG. 2.

In FIG. 2, the lens 5 is provided before the partial reflection mirror 8 in the optical path of the light projection. Instead, the same effect can be achieved by providing the lenses 5 behind the partial reflection mirror 8 as shown in FIG. 5. In FIG. 5, the same reference numbers as in FIG. 2 are used for indicating the corresponding members.

EXAMPLE 1

A fluorescent paper sheet was painted black at the peripheral portion with the central portion kept unpainted. This paper sheet was placed at the bottom of a black cup of 8 mm diameter having an opening at the top as shown in FIG. 1 with the center of the fluorescent paper sheet fixed at the center of the cup. The fluorescence was measured with the apparatus of FIG. 1 (employing a long fluorescent lamp as the light source).

Figure 3:
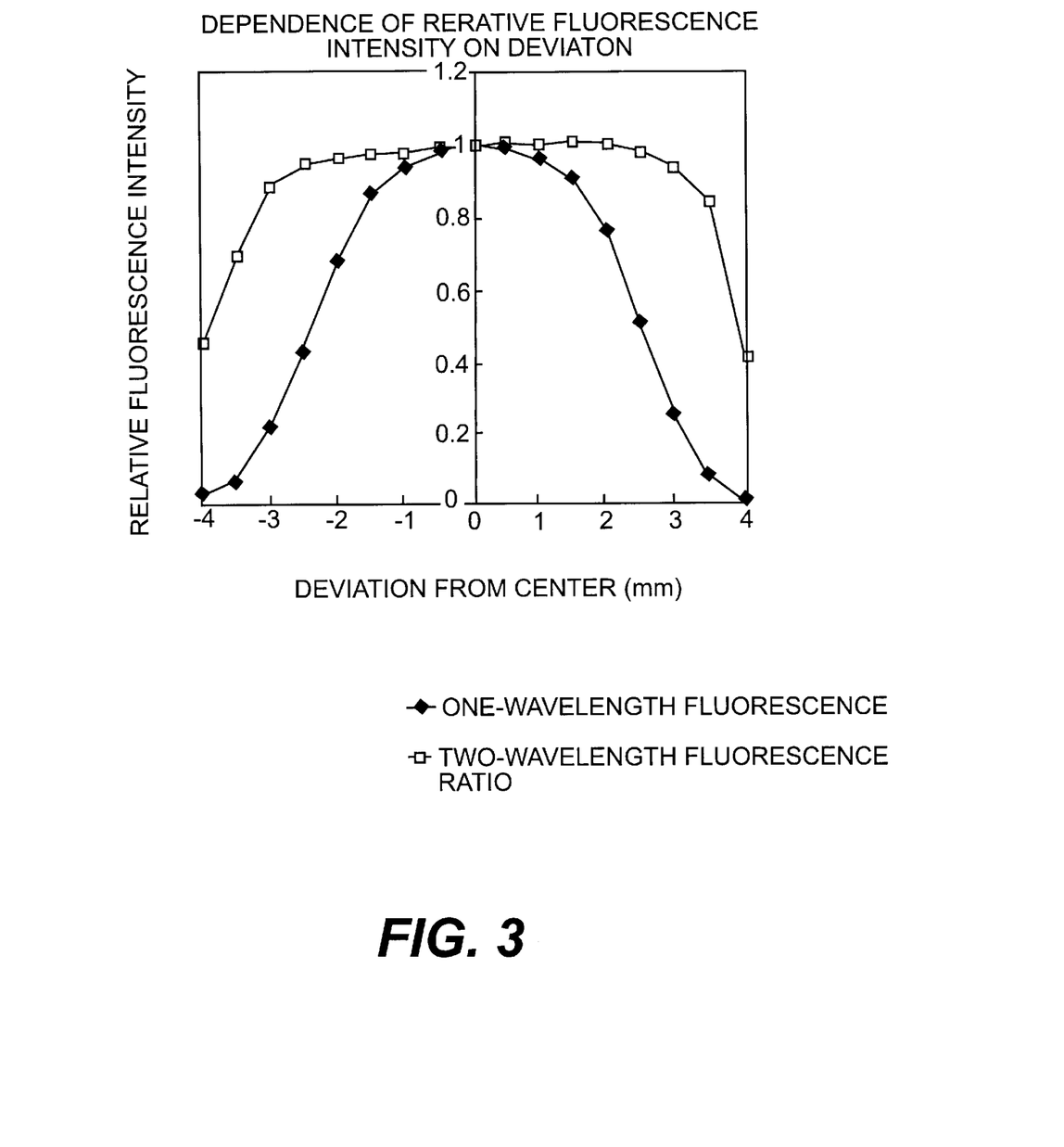
FIG. 3 shows the changes of output signals of the photodiode, when the optical axis of the optical measurement system of the fluorescence detection apparatus and the center of t he cell is displaced in a horizontal direction.

The measurements were conducted with the center of the black cup (center of the fluorescent paper sheet) to coincide approximately with the optical path of the light measurement system of the fluorescence detection apparatus, and with the center of the black cup deviated horizontally. The changes of the output signals of the photodiode 2 and the photodiode 3 were measured by changing the position of the cup. The ratios of the two signals (two-wavelength fluorescence ratio) were recorded for the deviation of the cup, taking the value with the black cup center placed the optical axis of the optical measurement system to be 100. For comparison, change of the output signals of the photodiode 2 (one-wavelength fluorescence) was recorded for the deviation of the cup, taking the value with the black cup center placed the optical axis of the optical measurement system to be 100. The results are shown in FIG. 3.

The results show that, in the comparative experiment, deviation of the cup of ±3 mm caused the drop of the signal by 70–80%, whereas according to the present invention, the same deviation caused the drop by 5–12% only. Thus, the influence of the positional deviation was confirmed to be remarkably decreased by the present invention.

EXAMPLE 2

Experiment was conducted to investigate the degree of variation of signals of the above formed fluorescent substance and the reference fluorescent substance from the photodiode as the detection element caused by the positional deviation of the reaction cell. The fluorescent substance, 4-methylumbelliferone (4MU), was formed from 4-methylumbelliferyl phosphate (4MUP: substrate) by alkaline phosphatase.

In a black-colored cup (reaction cell), were placed 220 $\mu$L of a sample solution containing 4000 nM 4-methylumbelliferone (4MU) as the objective fluorescent substance, and 0.1 mg/mL dansylalanine (DA) as the reference fluorescent substance. This cell was held in the cavity of intermittent delivery mechanism, and was delivered to the light measurement position of the optical measurement system of an enzyme immunoassay apparatus AIA1200 (manufactured by Tosoh Corporation). For sure holding and releasing of the reaction cell, a play of about 1.5 mm was provided in the cavity of the intermittent delivery mechanism for the reaction cell, which caused the positional deviation of the reaction cell from the optical axis of the optical measurement system.

In the example, for more measurement data, the apparatus shown in FIG. 1 was employed which is capable of excitation of fluorescent substances in plural cells with one lamp (light source), and two optical measurement systems of the same constitution were employed, and two reaction cells were delivered at the same time.

As the results, under the same conditions except the positional deviation, the variation coefficient (standard deviation/average) of the fluorescence intensity was as large as 23–24%, whereas the variation coefficient of the ratio of the fluorescence intensity of the 4MU to that of DA (dansylalanine) was as small as 1.06–1.83%. Therefore, by correcting the fluorescence intensity of 4MU (formed fluorescent substance) based on the fluorescence intensity of a reference fluorescent substance, DA (dansylalanine), the variation coefficient of the detected data of 4MU (measurement object) can be decreased remarkably to $\frac{1}{10}$ or below in comparison with that of a conventional detection method or apparatus, $\frac{1}{16}$ in the above experimental data, and higher accuracy can be achieved in fluorescence detection.

The advantages below can be achieved by the present invention.

In the first embodiment of the present invention, a pair of detection elements arranged to be optically equivalent relative to a light-separating element equalize substantially the intensity ratio of the fluorescence of the fluorescent at two detection elements, whereby the fluorescence can be detected with high accuracy by minimizing the influence of the positional deviation of the measurement cell in the optical measurement system.

In a modification of the above embodiment of the present invention, the first and the second condensing elements constituted respectively of a lens or the like are arranged in this order on the optical path of introducing the fluorescence emitted by the fluorescent substance in the reaction cell to the light-separating element such that the image of the fluorescent substance is formed by the first lens on the second lens and the image of the first lens is formed by the second lens on each of the first detection element and the second detection element, whereby the influence of the positional deviation of the reaction cell relative to the optical measurement system is further reduced effectively.

In the second embodiment of the present invention, and a modification thereof, the amount of an enzyme contained in an immunocomplex can be measured effectively by forming a fluorescent substance formed by enzyme activity by use of the above fluorescence detection apparatus.

In modifications of the second embodiment, a first optical information on intensity of fluorescence from a reference fluorescent substance exhibiting no change with time, and a second optical information on intensity of fluorescence from a formed fluorescent substance which changes in the quantity by enzyme reaction are measured by a pair of detection elements arranged to be optically equivalent, whereby optical measurement information can be obtained without influence of positional deviation of the cell containing a fluorescent substance.

What is claimed is:

1. A fluorescence detection apparatus having a light-separating element for transmitting a part of fluorescence emitted from a fluorescent substance by projection of excitation light and reflecting the rest of the fluorescence, and a first detection element and a second detection element for measuring fluorescence transmitted through or reflected by the light-separating element respectively at a selected wavelength, wherein said first and said second detection elements are arranged to be optically equivalent to each other relative to the light-separating element, wherein a first condensing element and a second condensing element are arranged in this order on the optical path for introducing the fluorescence emitted by the fluorescent substance to the light-separating element such that the image of the fluorescent substance is formed by the first condensing element on the second condensing element, and the image of the first condensing element is formed by the second condensing element on each of the first detection element and the second detection element.

2. The fluorescence detection apparatus according to claim 1, wherein the light-separating element is a partial reflection mirror selected from the group consisting of a dichroic mirror and a combination prism.

3. A fluorescence detection apparatus for measuring a fluorescent substance formed in a reaction cell by reaction caused by an enzyme contained in an immunocomplex, or a fluorescent substance contained in a complex formed by immunoreaction, comprising an optical light source system for projecting light for exciting a fluorescent substance in the cell, a light-separating element for transmitting a part of fluorescence emitted from a fluorescent substance and reflecting the rest of the fluorescence, and a pair of a first detection element and a second detection element for measuring selectively fluorescence transmitted through or reflected by the light-separating element, and a first condensing element and a second condensing element placed on the optical path for introducing the fluorescence of the fluorescent substance to the light-separating element wherein the first condensing element and the second condensing element are arranged such that the image of the fluorescent substance is formed by the first condensing element on the second condensing element, and the image of the first condensing element is formed by the second condensing element on each of the first detection element and the second detection element, and the pair of the detection elements are arranged to be optically equivalent to each other relative to the light-separating element.

4. The fluorescence detection apparatus according to claim 3, wherein the fluorescent substance formed in a reaction cell by reaction caused by the enzyme contained in the immunocomplex and a reference fluorescent substance emitting fluorescence without action of the enzyme in the cell are optically measured, and one of the detection elements measures the fluorescence intensity of the formed fluorescent substance at a selected fluorescence wavelength and the other of the detection elements measures the fluorescence intensity of the reference fluorescent substance at another selected fluorescence wavelength.

5. The fluorescence detection apparatus according to claim 3, wherein the fluorescent substance contained in a complex formed in a reaction cell by immunoreaction and a reference fluorescent substance emitting fluorescence in the cell are optically measured, and one of the detection elements measures the fluorescence intensity of the formed fluorescent substance at a selected fluorescence wavelength and the other of the detection elements measures the fluorescence intensity of the reference fluorescent substance at another selected fluorescence wavelength.

6. The fluorescence detection apparatus according to claim 3, wherein the apparatus further comprises a correction means for correcting the measured result of the fluorescence intensity of the fluorescence substance based on the measured result of the fluorescence intensity of the reference fluorescent substance.

7. The fluorescence detection apparatus according to any of claims 1 to 6, wherein the wavelength of the measurement is selected by a wavelength-selecting element provided on the optical path between the light-separating element and the detection element.

8. The fluorescence detection apparatus according to any of claims 1 to 6, wherein the light-separating element has a function of selecting the wavelength of the transmitted light.

9. The fluorescence detection apparatus according to any of claims 1 to 6, wherein the apparatus comprises a light condensing element for forming an image of the light source in the cell.

10. The fluorescence detection apparatus according to claim 7, wherein the apparatus comprises a light condensing element for forming an image of the light source in the cell.

11. The fluorescence detection apparatus according to claim 8, wherein the apparatus comprises a light condensing element for forming an image of the light source in the cell.

* * * * *